US00PP13457P2

(12) United States Plant Patent
Vardi et al.

(10) Patent No.: US PP13,457 P2
(45) Date of Patent: Jan. 7, 2003

(54) CITRUS TREE NAMED 'DITY'

(75) Inventors: Aliza Vardi, Ramat Gan (IL); Pinchas Spiegel-Roy, Ramat Gan (IL); Ahuva Frydman-Shani, Ramat Gan (IL); Avraham Elchanati, Holon (IL); Hana Neumann, Hemed (IL)

(73) Assignee: State of Israel - Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,480

(22) Filed: Nov. 20, 2000

(51) Int. Cl.[7] ..... A01H 5/00

(52) U.S. Cl. ..... Plt./202

(58) Field of Search ..... Plt./202

*Primary Examiner*—Kent L. Bell
(74) *Attorney, Agent, or Firm*—Barbara S. Kitchell

(57) ABSTRACT

A new variety of mandarin citrus is described that is distinguished by fruit having few or no seeds, a mid-late fruit ripening period and orange-red fruit when fully ripe.

2 Drawing Sheets

FIELD OF THE INVENTION

A new mandarin mandarin cultivar *Citrus reticulata* is described. The new variety, designated 'Dity' is desirable to the consumer because of the orange-red color of its fruit and to the commercial grower because of its appearance and mid-late fruit ripening.

BACKGROUND OF THE NEW PLANT

The present invention relates to a new and distinct variety of mandarin cultivar *Citrus reticulata* developed by inventors Aliza Vardi, Pinchas Spiegel-Roy, Ahuva Frydman-Shani, Avraham Elchanati and Hana Neumann in Bet Dagan, Israel from a selection of plants grown from irradiated bud wood of the cultivar 'Edit' (not patented).

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, assigned the denomination 'Dity', was to obtain a mid-late season ripening mandarin citrus with few of no seeds (0–3) per fruit. In the spring of 1989, about 300 buds of the mandarin cultivar, 'Edit', were irradiated at the Nahal Soreq Nuclear Center, Yavne, Israel, by exposure to 3.5 kh of gamma radiation from a Co60 source. Troyer and sour orange nucellar rootstocks were bud grafted with the individual buds of irradiated 'Edit' bud wood and labeled $mV_1$. Six to nine months after grafting the irradiated budwood, individual buds from the $mV_1$ plants were re-grafted on Troyer and Sour orange nucellar rootstocks to establish about 500 $mV_2$ plants.

Field planting was established from container grown $mV_2$ plants in the spring of 1992 and 1993. The first fruits were observed in December-January 1995–1996 and a second observation made during December–January of 1996–1997.

The selection '13/2/94', was distinguished from 'Edit' in having fruit with 0–3 seeds per fruit compared with 3–11 seeds for 'Edit' and in having low pollen fertility compared with 'Edit'. Typically, 3% of the pollen grains of 13/2/94 were stained by acetocarmine compared with 80% staining for 'Edit'.

SUMMARY OF THE INVENTION

Some characteristics of selection 13/2/94, designated 'Dity', compared with 'Edit' are shown in Table 1.

TABLE 1

| Tree | Fruit skin color | Peelability | Seeds/fruit | Pollen fertility[1] |
|---|---|---|---|---|
| 13/2/94 'Dity' | Orange 30B | Easy | 0–3 | 3% |
| 'Edit' | RHS30B | Easy | 3–11 | 80% |

[1]Estimated by Acetocarmine staining

The following is a detailed description of the new mandarin citrus variety based on observations made under typical Israeli grove conditions. Descriptions are based on observations of 3–4 year old plants grown in Bet Dagan, Israel. Color designations are based on comparisons determined from the R.H.S Colour Chart published by The Royal Horticultural Society.

The tree shape and fruit appearance are similar to that of 'Edit'. The tree is vigorous. Small thorns are usually present in the leafy part of branches. Main branches have an upright attitude and young shoots have no anthocyanin coloration at the tip. The bearing of the tree is regular and the productivity is relatively high, about the same as for 'Edit'. The canopy is moderately dense.

The bark of the young shoots is initially smooth and green gradually turning into a smooth brown-gray.

The leaf blades are firm, without undulation and concave in cross section. The leaves are similar to those of 'Edit' and are lancelolate, small to medium in size and without wings.

Th characteristics of the flowering and the flower parts are similar to those of 'Edit'. Flowering for both occurs at the end of March and beginning of April in Bet Dagan, Israel. Both 'Dity' and 'Edit' produce about the same number of flowers and flower drop for both occurs in June. Terminal flower buds have no anthocyanin coloration. Flowers are borne singly and have an average number of stamens (about 20) with complete style development. Anther color is pale yellow to white. Pollen fertility is low as indicated by the observation that only 2% of the pollen grains were stained with acetocarmine in a test conducted at the Agricultural Research Organization, the Volcani Center, Israel, as compared with about 80% for 'Edit' pollen grain.

The fruit is seedless or has few seeds, 0–3 seeds, even when optimal pollination conditions are employed. This compares with about 0–11 seeds per fruit in 'Edit'. In other respects the fruit characteristics of 'Dity' are in the range of the parent cv. 'Edit'. The fruit shape is oblate and medium-sized. When 50 fruits were measured, the fruit had an average weight 94.6 grams, an average height 44.7 mm, and an average diameter of 65 mm. The fruit has a moderately depressed stalk end. The fruit surface is usually smooth with an orange color, RHS 30B, on The Royal Horticultural Society of London Colour Chart, and bears an average number of conspicuous rind oil glands (30 per $cm^2$). Fruit ripening does not differ from outside of the canopy to the inside, but the fruit color of the outside canopy is a little brighter compared to the fruit color of the inside canopy. There is no persistence of the style and the areola is not completely developed. A navel is absent or rare. The rind is thin and easy to peel.

The color of the albedo is white and the flesh is orange in color. The fruit contains 9–11 segments and is very juicy. The external color of the seeds (when fresh) and dry is ivory. The internal seed coat is white and the cotyledons are white. Monoembryonic seeds are present. The seed sizes, shape and texture are similar to that of the parent 'Edit'. The fruit reaches maturity at the beginning of December to the end of January. The ripening of the fruit on the tree and within the fruit is uniform. Fruit remaining on the tree does not regreen and begins to lose quality at the beginning of February. If there is a heavy crop and the fruits are not picked during the ripening season, the tree may become alternate bearing (produces less fruit the following season). Pre-harvest drop of both developed and undeveloped fruit is similar to that of the parent cv. 'Edit'.

DESCRIPTION OF THE PHOTOGRAPHS

Sheet 1 shows the whole tree and canopy shape of the new variety.

Sheet 2 illustrates the exterior of the new fruit variety 'Dity' as well as transverse midsections in a plane substantially perpendicular to the axis.

DESCRIPTION OF THE NEW TREE

The following is a detailed description of the new mandarin citrus variety 'Dity' based on observations made under typical Israeli grove conditions.

Tree:

*Origin.*—Irradiation of cv. 'Edit'.
*Classification.*—Botanical: *Citrus reticulata* hybrid. Common: Mandarin citrus. Cultivar: 'Dity'.
*Shape.*—Shape is rounded when pruned.
*Thorns.*—Small, 1–3 mm length.
*Branching.*—Upright.
*Canopy.*—Moderately dense.
*Bark.*—Immature: Smooth, green, RHS 139B. Mature: Smooth, greyed-green, RHS 197B.
*Leaf.*—Size: average 76 mm length, average 32 mm wide. Leaf blade: Firm, no undulation, concave cross section. Color: RHS 146A upper; RHS 146C lower. Shape: Lanceolate.
*Petioles.*—Average 8 mm length, average 1.5 mm diameter. Color: RHS 146A.
*Habit.*—Moderately vigorous.
*Height.*—2.3–3 m.
*Trunk.*—Average 37 cm in diameter at 20 cm above ground.
*Disease resistance.*—No particular suseptibility or resistance observed.
*Winter hardiness.*—Winter temperature in Bet Dagan, Israel averages 4–7 degrees Centigrade.

Flower:

*Petal color.*—RHS 155B.
*Petal number.*—5.
*Flowering period.*—End of March to beginning of April (Israel).
*Flower drop.*—April.
*Stamens.*—Approximately 20 with complete style development.
*Anther color.*—Pale yellow to white, RHS 10C.
*Pollen fertility.*—Low, 3% by acetocarmine staining.
*Anthocyanin coloration.*—No coloration.

Fruit:

*Shape.*—Oblate.
*Size.*—Medium.
*Weight.*—94.6 g (average of 50 fruits).
*Height.*—44.7 mm.
*Diameter.*—Average 65 mm.
*Surface color.*—Orange RHS 30B.
*Rind oil gland.*—Moderately conspicuous (30 per $cm^2$).
*Style.*—No persistence.
*Navel.*—Absent or rare; if present, they are very small and attached to the peel.
*Rind.*—Thin and easy to peel.
*Albedo.*—White, RHS 12D.
*Areola.*—Incompletely developed.
*Fruit segments.*—9–11.
*Color of flesh.*—Orange, RHS 28B.
*Time to maturity.*—December–January (Israel).
*Productivity.*—60 kg/tree per season.
*Fruit extract.*—(Quality tested Jan. 20, 1997). Total soluble solids (TSS) 12.8%. Acid content: 1.57%. TSS/acid ratio 8.16. Flavor: Pleasant.

Seeds:

*Color.*—External: Ivory (dry, fresh) RHS 158A. Internal: White, RHS 164A.
*Cotyledons.*—Green-white RHS 157C.
*Embryony.*—Monoembryonic.

The tree and its fruit as described herein may vary somewhat in certain characteristics due to climatic and/or soil conditions under which the variety is grown.

What is claimed is:

1. A new and distinct variety of *Citrus reticulata* tree substantially as herein described and shown.

* * * * *

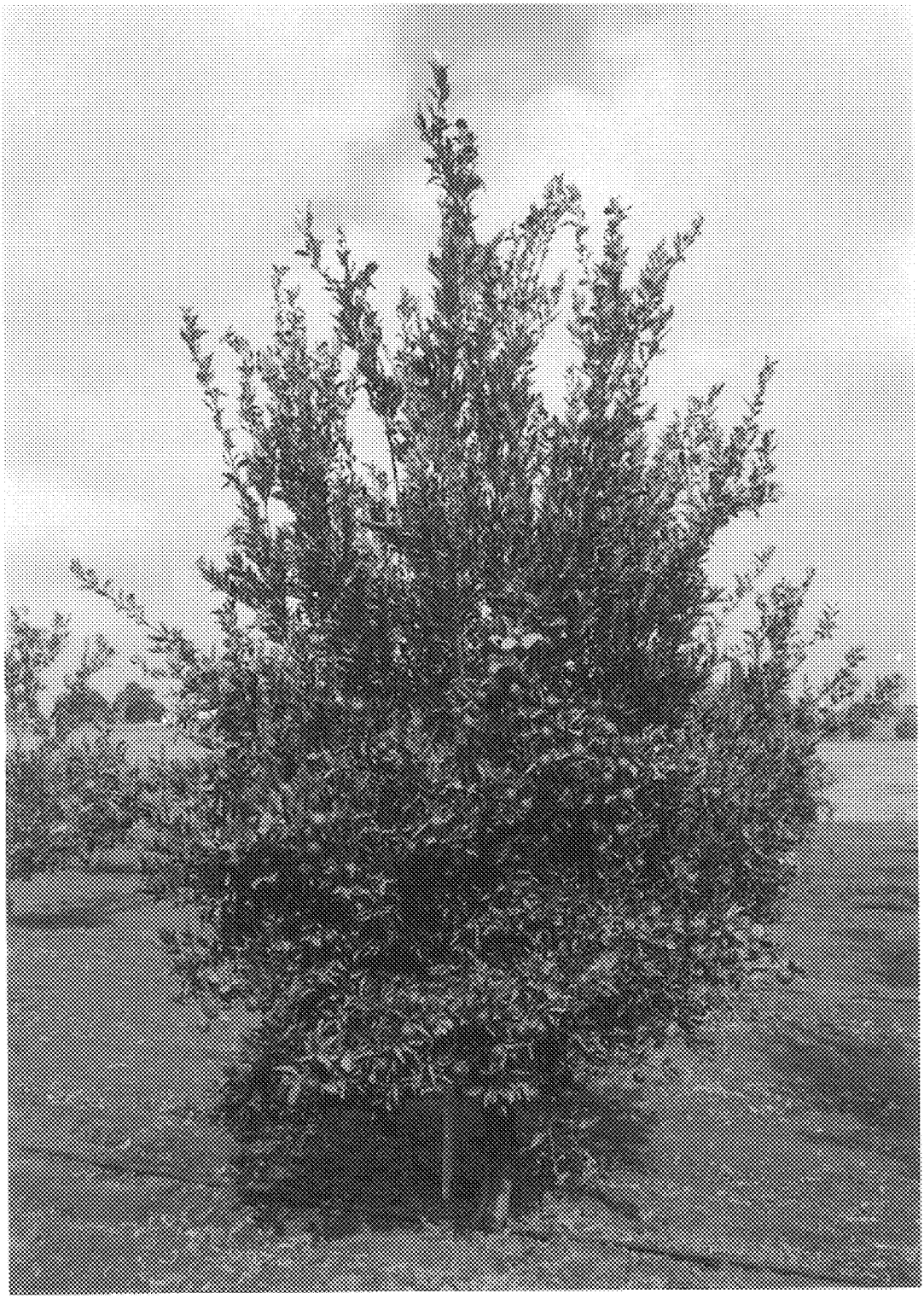

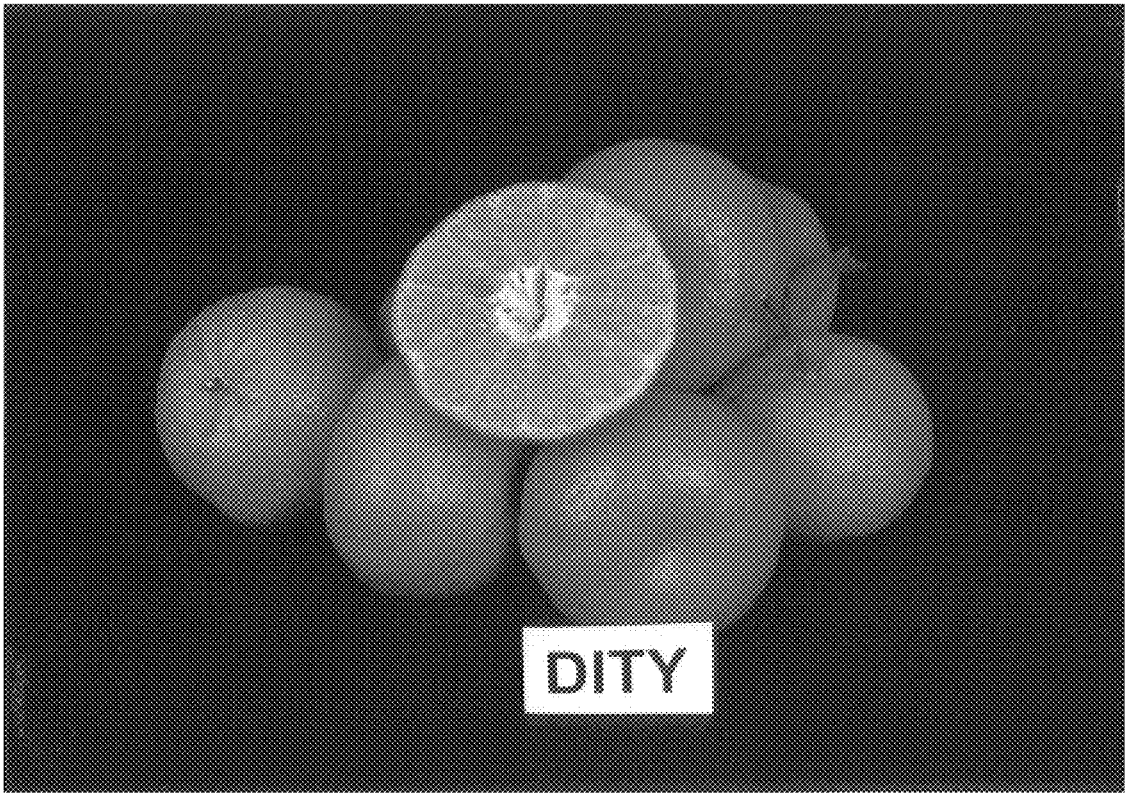
DITY